(12) United States Patent
Chen et al.

(10) Patent No.: US 12,048,929 B2
(45) Date of Patent: Jul. 30, 2024

(54) ARRAY PLATFORM FOR THREE-DIMENSIONAL CELL CULTURING AND DRUG TESTING AND SCREENING

(71) Applicants: NATIONAL TSING HUA UNIVERSITY, Hsinchu (TW); TAIPEI MEDICAL UNIVERSITY, Taipei (TW)

(72) Inventors: Yu-Chen Chen, New Taipei (TW); Han-Jung Liao, Wuqiu Township (TW); Kang-Yun Lee, Taipei (TW); Shu-Chuan Ho, New Taipei (TW); Weilun Sun, New Taipei (TW); Cheng-Hsien Liu, Hsinchu (TW)

(73) Assignees: NATIONAL TSING HUA UNIVERSITY, Hsinchu (TW); TAIPEI MEDICAL UNIVERSITY, Taipei (TW)

( * ) Notice: Subject to any disclaimer, the term of this patent is extended or adjusted under 35 U.S.C. 154(b) by 361 days.

(21) Appl. No.: 17/393,147

(22) Filed: Aug. 3, 2021

(65) Prior Publication Data

US 2022/0395830 A1     Dec. 15, 2022

(30) Foreign Application Priority Data

Jun. 15, 2021   (TW) ................................ 11012173.0

(51) Int. Cl.
*B01L 3/00*     (2006.01)
*C12M 1/12*     (2006.01)
(Continued)

(52) U.S. Cl.
CPC ... *B01L 3/502753* (2013.01); *B01L 3/502715* (2013.01); *C12M 23/16* (2013.01);
(Continued)

(58) Field of Classification Search
None
See application file for complete search history.

(56) References Cited

U.S. PATENT DOCUMENTS

| 10,233,415 | B1 * | 3/2019 | Mathur | ................ G01N 33/502 |
| 2011/0086382 | A1 * | 4/2011 | Marx | ..................... C12M 23/16 |
| | | | | 435/325 |
| 2020/0392440 | A1 * | 12/2020 | Nieh | .................. G01N 33/5008 |

FOREIGN PATENT DOCUMENTS

| CN | 206502830 U | * | 9/2017 | |
| CN | 109234163 A | * | 1/2019 | ............ C12M 23/16 |
| CN | 110373321 A | * | 10/2019 | |

OTHER PUBLICATIONS

Ahadian et al. "Facile and rapid generation of 3D chemical gradients within hydrogels for high-throughput drug screening applications", Biosensors and Bioelectronics 59 (2014) 166-173. (Year: 2014).*

(Continued)

*Primary Examiner* — William H. Beisner
(74) *Attorney, Agent, or Firm* — Birch, Stewart, Kolasch & Birch, LLP

(57) ABSTRACT

An array platform for three-dimensional cell culturing and drug testing and screening is disclosed. In the array platform, a hydrogel-cell mixture injection area is configured to inject a plurality of kinds of hydrogel-cell mixtures. Cell observation areas are connected to the hydrogel-cell mixture injection area. Electrodes are disposed under the cell observation areas and automatic cell quantification and three-dimensional cell co-arrangement of the plurality of kinds of hydrogel-cell mixtures in the cell observation areas through the electrodes to imitate a structure of body's tissues. A drug injection area is configured to inject a plurality of kinds of drugs. Drug combination generators respectively correspond to the cell observation areas and are connected to the drug (Continued)

injection area. Each drug combination generator has a microfluidic channel structure and configured to generate drug combinations according to the plurality of kinds of drugs.

9 Claims, 5 Drawing Sheets

(51) Int. Cl.
    *C12M 1/34*     (2006.01)
    *C12M 1/36*     (2006.01)
    *C12M 3/06*     (2006.01)
    *C12N 5/00*     (2006.01)

(52) U.S. Cl.
    CPC ............ *C12M 25/14* (2013.01); *C12M 41/46* (2013.01); *C12M 41/48* (2013.01); *C12N 5/0068* (2013.01); *B01L 2300/0645* (2013.01); *B01L 2300/0819* (2013.01); *B01L 2300/0883* (2013.01); *B01L 2400/0424* (2013.01); *C12N 2513/00* (2013.01)

(56) References Cited

OTHER PUBLICATIONS

Chan et al. "Accelerating drug discovery via organs-on-chips", Lab Chip, 2013, 13, 4697-4710. (Year: 2013).*

Tomecka et al. "Microsystem with micropillar array for three- (gel-embaded) andtwo-dimensional cardiac cell culture", Sensors and Actuators B 254 (2018) 973-983. (Year: 2018).*

Hsiung et al. "A planar interdigitated ring electrode array via dielectrophoresis for uniform patterning of cells." Biosensors and Bioelectronics 24 (2008) 869-875. (Year: 2008).*

* cited by examiner

ARRAY PLATFORM FOR THREE-DIMENSIONAL CELL CULTURING AND DRUG TESTING AND SCREENING

BACKGROUND OF THE INVENTION

1. Field of the Invention

The invention relates to cell culturing; in particular, to an array platform for three-dimensional cell culturing and drug testing and screening.

2. Description of the Prior Art

In general, cell culturing is very important for testing drug combinations. However, most of the current cell culturing technologies are mainly to culture cells in orifice plates. Although it has advantages of easy control and operation, it also faces problems of mutual influence between different types of cells and difficult to imitate its histological composition due to disordered arrangement of cells. Therefore, it is still unable to effectively simulate the cell growth environment, resulting in that the bionicity of cell culturing still needs to be improved.

In addition, animal experiments and human experiments are currently used as drug test platforms in biomedicine, and its test time is often very long. In addition, the conventional drug testing platform only focuses on testing a single drug at one time, ignoring the efficacy that can be achieved by compound drugs or the curative effect of the compound drugs that is better than that of a single drug. As a result, it is conventionally impossible to mix multiple types of drugs within biomedical chips, and it is impossible to test the influence of different drug combinations in large quantities. Therefore, the drastic improvement of efficiency and range for drug screening is also an urgent issue.

Regarding the quantification of the number of cells in biochips, most of them are still manual counting, which is easy to cause uneven numbers and is difficult to control, and it is easy to cause problems such as unevenly dispersion during the process of injecting cells into the chip or difficulty in observation due to insufficient cell numbers, leading to poor cell quantitative stability and density, which needs to be improved urgently.

Please refer to FIG. 1 and FIG. 2 simultaneously. According to the prior art, if different kinds of hydrogel-cell mixtures need to be light-cured in the same chamber, the required steps are relatively complicated, and a photomask and multiple hydrogel inlets and outlets are required.

For example, if there are three different hydrogel-cell mixtures, the conventional light-curing method needs to perform the following steps of (S10) injecting a first hydrogel-cell mixture into a culturing chamber; (S11) adjusting a position of a photomask to light-cure hydrogels in area A; (S12) rinsing off excess hydrogels not light-cured in areas B and C; (S13) injecting a second type of hydrogel-cell mixture into the culturing chamber; (S14) adjusting the position of the photomask to light-cure hydrogels in area B; (S15) rinsing off excess hydrogels not light-cured in area C; (S16) injecting a third type of hydrogel-cell mixture into the culturing chamber; and (S17) adjusting the position of the photomask to light-cure hydrogels in the area C.

Since the microstructure technology may not be able to stably separate different kinds of mixtures to be close enough to allow the effective transfer of cytokines between the mixtures, and the different kinds of mixtures cannot be mixed with each other, which makes observation difficult. In addition, if there are multiple types of cells needed to be light-cured, the final light-cured cells may be lost due to the long waiting time, so there is still room for improvement in their timeliness and operability.

SUMMARY OF THE INVENTION

Therefore, the invention provides an array platform for three-dimensional cell culturing and drug testing and screening to effectively solve the above-mentioned problems in the prior art.

A scope of the invention is to propose an in vitro cell automatic co-arrangement system, its purpose is to provide an observation platform for three-dimensional cell automatic co-arrangement, and use liquid dielectrophoresis and dielectrophoresis technology to complete automatic combination of drugs and automatic arrangement and quantification of cells, and combined with microfluidic technology to reduce costs and solve related problems such as in vitro cell bionics and drug screening.

A scope of the invention is to propose a three-dimensional drug screening platform for automatic cell arrangement and quantification, which can simultaneously integrate functions of cell co-cultivation, dynamic injection, three-dimensional hydrogel environment, automatic cell quantification and alignment, and drug screening technologies to perform integration and design to simplify operation steps and chip manufacturing process; it can use the hydrogel to imitate the extracellular matrix to construct cell structure to achieve a more conducive environment for cell growth; and the dielectrophoresis technology can be used to manipulate the number of cells needed for the hydrogel quantification to simulate the status of patients in the first to fourth stages of cancer to achieve the effect of personalized medicine; it can also use dielectrophoresis technology to arrange multiple types of cells to mimic the structure of tissues in the body, thereby improving the biomimetic of the follow-up drug screening platform to make the test results closer to the needs of patients; it can also use the drug screening platform to construct different drug combinations to test the most suitable drug combination for patients, so it can effectively assist the hospital in preliminary screening of drug combinations.

The array platform for three-dimensional cell culturing and drug testing and screening of the invention includes an upper microfluidic channel terminal and a lower electrode terminal. The microfluidic channel terminal realizes the production of different drug combinations, and the electrode terminal performs multiple cell quantification and three-dimensional automatic arrangement. An injection terminal of the upper layer of hydrogel-cell mixture radiates from a center to a cell observation area. In the cell observation area, electrodes are used to control different amounts of different types of cells and subsequently co-arrange them, and three-dimensional hydrogel light-curing is used. The periphery are drug injection terminal and buffer injection terminal, and the drugs are injected and different drug combinations are generated with a microfluidic channel structure.

A specific embodiment of the invention is an array platform for three-dimensional cell culturing and drug testing and screening. In this embodiment, the array platform for three-dimensional cell culturing and drug testing and screening includes a hydrogel-cell mixture injection area, a plurality of cell observation areas, a drug injection area and a plurality of drug combination generators. The hydrogel-cell mixture injection area is configured to inject a plurality of kinds of hydrogel-cell mixtures. The plurality of cell observation areas is connected with the hydrogel-cell mixture injection area. Electrodes are disposed under the plurality of cell observation areas, and the plurality of hydrogel-cell mixtures in the plurality of cell observation areas are automatically quantified and three-dimensional cell co-arranged through the electrodes to imitate a structure of tissues in body. The drug injection area is configured to inject a plurality of kinds drugs. The plurality of drug combination generators corresponds to the plurality of cell observation areas respectively and are all connected with the drug injection area. Each of the drug combination generators has a microfluidic channel structure and configured to generate a plurality of drug combinations according to the plurality of drugs.

In an embodiment, the array platform for three-dimensional cell culturing and drug testing and screening further includes a culturing solution injection area and a culturing solution recycling area. The culturing solution flowing out from the culturing solution injection area flows through the plurality of cell observation areas through a microfluidic channel to wash off excess hydrogel and cells, and then flows to the culturing solution recycling area.

In an embodiment, a shape of the microfluidic channel and an order and a winding method of the microfluidic channel passing through the plurality of cell observation areas are variable.

In an embodiment, the array platform for three-dimensional cell culturing and drug testing and screening further includes micropillars configured to prevent the hydrogels from being washed away during dynamic injection.

In an embodiment, the array platform for three-dimensional cell culturing and drug testing and screening further includes a buffer solution injection area connected to the drug combination generator and configured to inject buffer solution.

In an embodiment, when the plurality of hydrogel-cell mixtures has been arranged in a specific position by the electrode using liquid dielectrophoresis technology, the plurality of hydrogel-cell mixtures is directly cured by light in a large area without a photomask to imitate a structure of body tissues.

In an embodiment, size and response frequency of an electric field generated by the electrode are used to imitate a composition of cancer tumors of different progressions and automatically arrange the plurality of kinds of cells in the plurality of kinds of hydrogel-cell mixtures, thereby simulating characteristics of mutual influence among the plurality of kinds of cells during a growth process to improve shortcomings of cultivating a single cell.

In an embodiment, the size of the electrode pattern is used to distinguish the disease progression of body tissues.

In an embodiment, an arrangement of the plurality of cell observation areas is symmetrical to the hydrogel-cell mixture injection area, and the hydrogel-cell mixture injection area is connected to the plurality of cell observation areas radially outward.

In an embodiment, the plurality of drug combinations generated by the drug combination generator are tested by the mimicked structure of body tissue, so that the results of the drug test can be close to the patient's needs and the most suitable drug combination required by the patient is screened out from the plurality of drug combinations.

In an embodiment, after a semi-circular hydrogel in the plurality of cell observation areas is cured by light, a number and a distance of cell migration in the light-cured semi-circular hydrogel can be quantified free from an effect of gravitational force to measure a distance of a lateral displacement of the cell and its migration distance at different time points, so as to effectively simulate an effect of different drugs and different reaction times on a tumor microenvironment in human body.

Compared with the prior art, the array platform for three-dimensional cell culturing and drug testing and screening proposed in the invention can achieve the following advantages and effects:

(1) Construction of tumor microenvironment: using microfluidic structure combined with three-dimensional hydrogel and automatic co-arrangement of different types of cells to co-culture different types of cells to completely simulate the tumor microenvironment in the body of the patient.

(2) Construction of the cell co-arrangement platform: design by calculating the effects of the size and frequency of the electric field generated by the electrode, so that it can imitate the different cell composition of histology, automatically arrange the plurality kinds of cells, and simulate the mutual influence of the plurality kinds of cells in the growth process to improve the shortcomings of single cell culturing.

(3) Automatically capture and quantify the number of cells: different numbers and properties of cells can be captured through differences in electrode patterns, which can be applied to simulate tumor sizes of different degrees.

(4) Dynamic injection system: The dynamic injection system is used to replace the culturing medium, so that the cells can grow effectively.

(5) Quantification of the number and distance of cell migration: by curing the semi-circular hydrogel, subsequent experimental results, such as the number and distance of immune cell migration, can be quantified, compared to the conventional holes plate test that cells migrate vertically from top to bottom, through this design, the invention can effectively avoid the influence of gravitation and measure the lateral displacement distance of immune cells and their migration distance at different time points, so as to simulate the effects on the tumor microenvironment under different drugs and different reaction times in human body, therefore, the efficiency and accuracy of drug screening can be greatly improved.

The advantage and spirit of the invention may be understood by the following detailed descriptions together with the appended drawings.

BRIEF DESCRIPTION OF THE APPENDED DRAWINGS

DETAILED DESCRIPTION OF THE INVENTION

Figure 1:
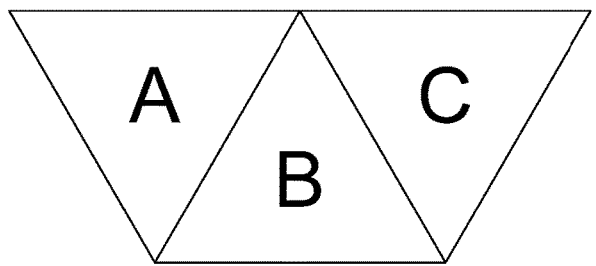
FIG. 1 is a schematic diagram showing three different hydrogel-cell mixtures in a chamber at the same time.
Figure 2:
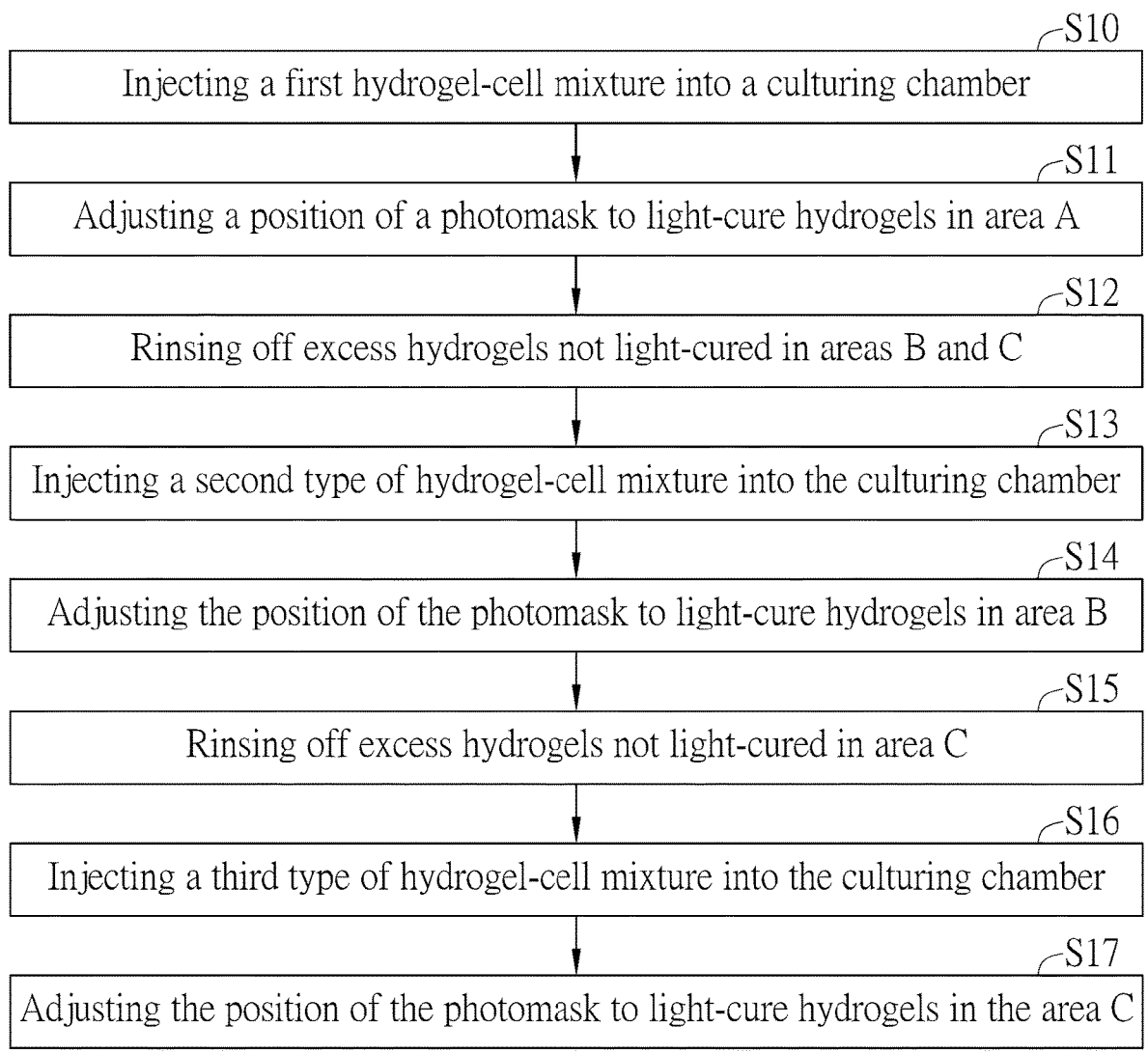
FIG. 2 shows a flow chart of a conventional method for photocuring three different hydrogel-cell mixtures in a chamber.

Exemplary embodiments of the invention are referenced in detail now, and examples of the exemplary embodiments are illustrated in the drawings. Further, the same or similar reference numerals of the components/components in the drawings and the detailed description of the invention are used on behalf of the same or similar parts.

One of the scopes of the invention is to propose an in vitro cell automatic co-arrangement system, its purpose is to provide an observation platform for three-dimensional cell automatic co-arrangement, and to use liquid dielectrophoresis and dielectrophoresis technology to complete the automatic combination of drugs and cell automatic arrangement, and combined with microfluidic technology to reduce costs and solve related problems such as in vitro cell bionics and drug screening.

One of the scopes of the invention is to propose a three-dimensional drug screening platform for automatic cell alignment and quantification, which can simultaneously integrate cell co-culturing, dynamic injection, three-dimensional hydrogel environment, automatic cell quantification and alignment, and drug screening technologies. The function is integrated and designed to simplify the operation steps and the chip manufacturing process; it can use the hydrogel to imitate the extracellular matrix to construct the cell structure to achieve a more conducive environment for cell growth; and the dielectrophoresis technology can be used to manipulate the cells needed for the hydrogel quantification to simulate the status of patients with stage 1 to stage 4 of cancer, the effect of personalized medicine can be achieved; it can also use dielectrophoresis technology to arrange a plurality of types of cells to imitate the structure of body tissues, thereby improving the biomimetic of follow-up drug screening platform, so that the test results can be closer to the needs of patients; it can also use the drug screening platform to construct different drug combinations, so as to screen out the most suitable drug combinations for patients, so it can effectively assist the hospital in drug delivery Preliminary screening of combinations.

The use of orifice plates and culturing plates is the current mainstream culturing method of biological cell culturing, but they are different from the growth of human tissues to a certain extent, and it is difficult to reproduce the dynamics of cells in the human microenvironment; while screening drug by using animal models is time-consuming and has poor efficiency. Animal cells are different from humans and have ethical reasons. Human testing is most consistent with the growth environment of cells in the human body. However, cancer patients are ignored here. Therefore, this chip combines a plurality of technologies to use patient's cells for subsequent three-dimensional culturing, cell quantification and arrangement, effectively simulating the human tumor microenvironment, and mimicking the tumor growth status of patients with stage 1 to stage 4 of cancer to perform following drug combination screening and testing.

Although there have been previous biomedical chips combined with dielectric wetting technology to control the three-dimensional hydrogel to reach the target area, it is impossible to establish different drug combinations in the chip for screening; although the biomedical chip using dielectrophoresis cell array technology alone can effectively arrange the cells tightly, it is impossible to manipulate the hydrogel to form a specific shape or reach the target area. Therefore, the invention combines both liquid dielectrophoresis and dielectrophoresis techniques to improve the lack of existing technologies, so that the cells can be quantified and then co-arranged and co-cultivated.

Figure 3:
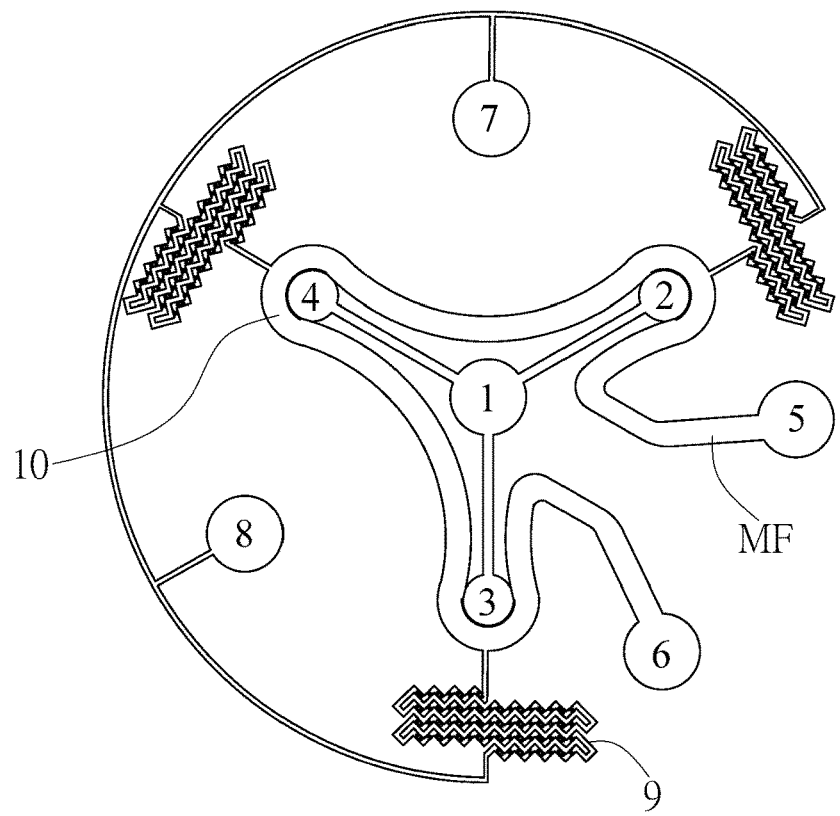
FIG. 3 is an overall schematic diagram of a three-dimensional drug screening platform for automatic cell arrangement and quantification according to a preferred embodiment of the present invention.

Please refer to FIG. 3, which illustrates an overall schematic diagram of a three-dimensional drug screening platform for automatic cell arrangement and quantification according to a preferred embodiment of the invention.

As shown in FIG. 3, the three-dimensional drug combination screening platform for automatic cell arrangement and quantification of the invention can include a hydrogel-cell mixture injection area 1, a plurality of cell observation areas 2~4, a culturing solution injection area 5, a culturing solution recycling area 6, a drug injection area 7, a buffer solution injection area 8, a drug combination generator 9 and microcolumns 10.

Figure 4:
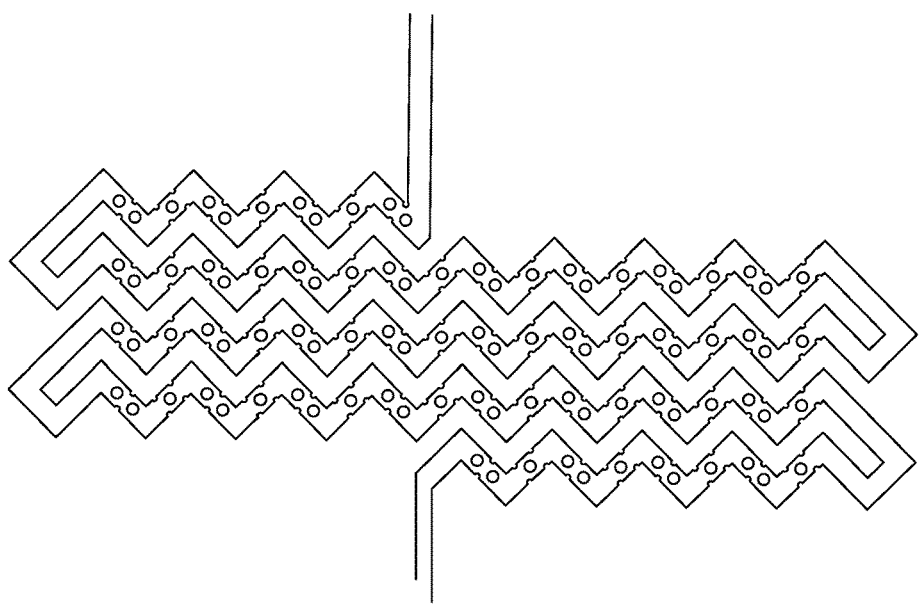
FIG. 4 shows a schematic diagram of an embodiment of the drug combination generator.
Figure 7A:
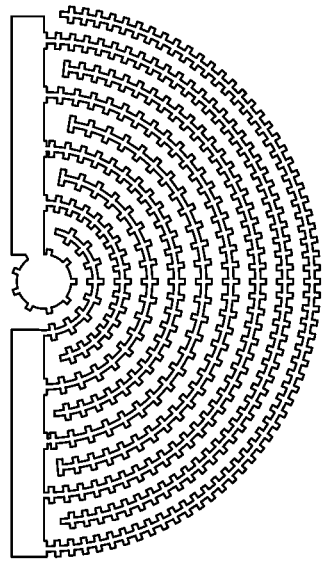
FIG. 7A to FIG. 7C are schematic diagrams showing the use of electrode size to distinguish cancer progression.
Figure 7B:
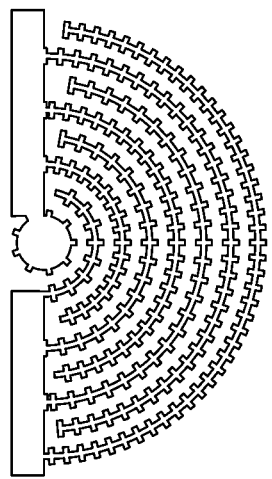
Figure 7C:
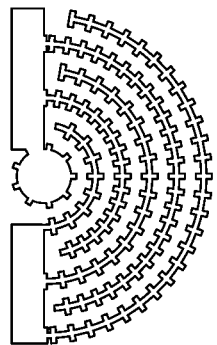

It should be noted that the drug combination generator 9 has a microfluidic channel structure and its embodiment is shown in FIG. 4, but not limited to this. In addition, electrodes are disposed on the lower plates of the plurality of cell observation areas 2~4, and its embodiments are shown in FIG. 7A-FIG. 7C, but not limited to this. The arrangement of the plurality of cell observation areas 2~4 is symmetrical to the hydrogel-cell mixture injection area 1, and the hydrogel-cell mixture injection area 1 is connected to the plurality of cell observation areas 2~4 radiating outward.

When the hydrogel-cell mixture flows from the hydrogel-cell mixture injection area 1 to the plurality of observation areas 2~4, since electrodes are disposed at the lower plates of the plurality of cell observation areas 2~4, in the invention, the dielectrophoresis technology can be used to automatically quantify and arrange the cells in the cell observation area through the electrode, so as to simulate the tumor microenvironment of cancer patients.

Figure 5:
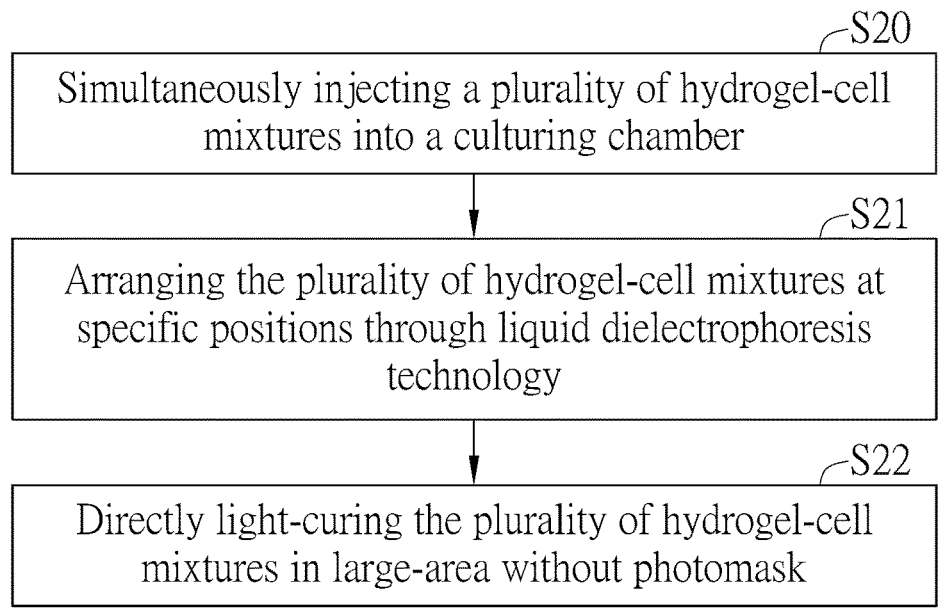
FIG. 5 shows a flow chart of a method for photocuring a plurality of different hydrogels on a large area at the same time directly in a chamber according to a preferred embodiment of the present invention.

For example, as shown in FIG. 5, the hydrogel photocuring method disclosed in the invention can include the following steps: (S20) simultaneously injecting a plurality of hydrogel-cell mixtures into a culturing chamber; (S21) arranging the plurality of hydrogel-cell mixtures at specific positions through liquid dielectrophoresis technology; and (S22) directly light-curing the plurality of hydrogel-cell mixtures in large-area without photomask. Thereby, the hydrogel photocuring method disclosed in the invention takes short time and is easy to operate, and can effectively improve the survival rate of all cells after photocuring.

Next, the invention can also use the culturing solution injection area 5 to inject the culturing solution through the microfluidic channel MF and flow through the plurality of cell observation areas 2~4 to wash off excess hydrogel and cells, and finally flow to the culturing solution recycling area 6. The shape of the microfluidic channel MF (such as a symmetrical shape, but not limited to this) and the order and winding method of passing through the plurality of cell observation areas 2~4 are variable, so they can be determined according to practical needs. The microcolumns 10 are used to stop the hydrogel. In addition, the drug injection area 7 and the buffer solution injection area 8 disposed on the periphery are used to inject drugs and buffer solutions respectively, and to generate different drug combinations through the drug combination generator 9 having the microfluidic channel structure.

It should be noted that the three-dimensional drug combination screening platform for automatic cell arrangement and quantification of the invention has a double-layer structure including an upper microfluidic channel terminal and a lower electrode terminal. Among them, the upper microfluidic channel terminal is used to realize the generation of different drug combinations and the lower electrode terminal is used to perform quantification and three-dimensional automatic arrangement on a plurality of cells.

As shown in FIG. 3, the hydrogel-cell mixture radiates outward from the hydrogel-cell mixture injection area 1 located in the center to the plurality of cell observation areas 2~4. The plurality of cell observation areas 2~4 use liquid dielectrophoresis technology to make the hydrogel reach the target area through the lower electrode terminal and control different numbers of different types of cells through the dielectrophoresis technology, and then use the three-dimensional hydrogel light-curing technology to directly perform large-area light-curing without photomask. The drug injection area 7 and the buffer solution injection area 8 disposed on the periphery are used to inject drugs and buffer solutions respectively, and generate different drug combinations through the drug combination generator 9 having the microfluidic channel structure.

It should be noted that the liquid dielectrophoresis technology used in the invention can greatly simplify the complicated steps of photocuring on different hydrogel-cell mixtures in the same chamber, so that it can be completed in one step, so different kinds of hydrogel-cell mixtures can be injected sequentially through a single inlet and outlet of the hydrogel, and then the lower electrode is used to arrange the different kinds of hydrogel-cell mixtures at one time, and light-curing in a large area can be directly performed without photomask, so it requires a shorter time and is easy to operate, and can effectively improve the survival rate of all cells after light-curing.

In addition, the liquid dielectrophoresis technology used in the invention can pattern the hydrogel to a very fine degree, thereby effectively improving the bionicity of the tumor microenvironment simulating cancer patients, and it can also make different kinds of hydrogel-cell mixtures will not mix with each other and are easy to observe.

Figure 6:
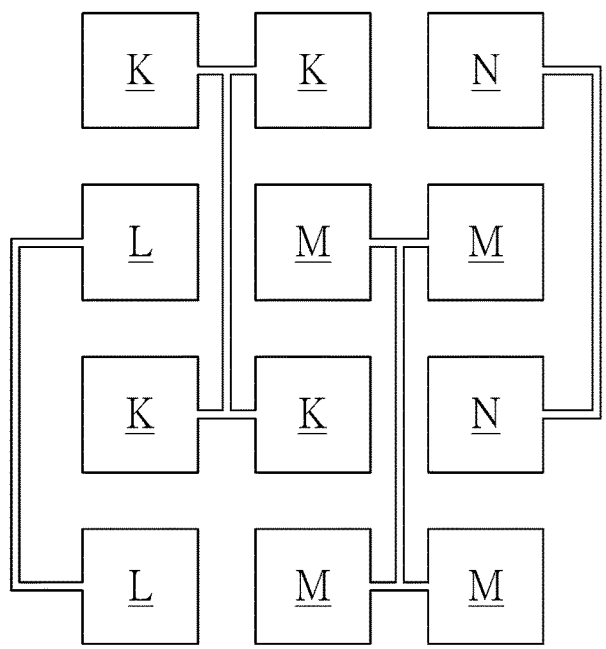
FIG. 6 shows a schematic diagram of the lower electrode area in the chip, which can simultaneously cultivate more than one hydrogel-cell mixture and observe the cell interaction under different drug combinations.

Next, please refer to FIG. 6. FIG. 6 illustrates a schematic diagram of an embodiment of the lower electrode area in the chip. As shown in FIG. 6, in this embodiment, if viewed from left to right, electrode partitions of the first straight row are KLKL from top to bottom, the electrode partitions of the second straight row are KMKM from top to bottom, and the electrode partitions of third straight electrode partition is NMNM from top to bottom. The same electrode partitions are connected to each other (for example, all electrode partitions K are connected to each other, and the rest can be deduced by analogy). In this way, the liquid dielectrophoresis technology of the invention can simultaneously cultivate a plurality of hydrogel-cell mixtures through the electrode partitions, and observe the cell interactions under different drug combinations.

Next, please refer to FIG. 7A-FIG. 7C. FIG. 7A-FIG. 7C show electrode structures with different sizes respectively. The invention can use the electrode size to distinguish the progress (such as the first stage to the fourth stage) of diseases (such as cancer tumors) in tissues (such as lungs) in the body, but not limited to this.

Figure 8:
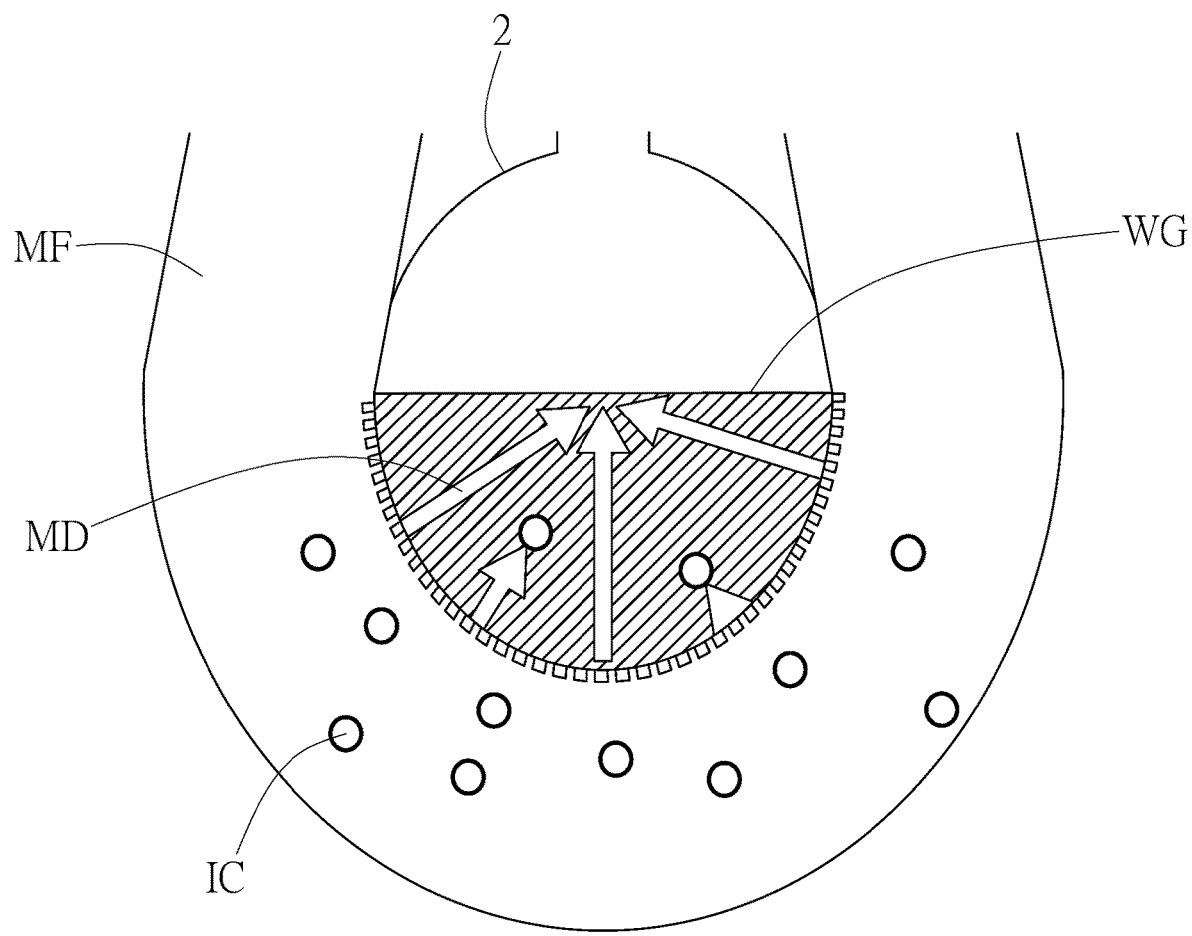
FIG. 8 is a schematic diagram showing that the number and distance of migration of immune cells can be quantified by the solidification of the semi-circular hydrogel.

In another embodiment, as shown in FIG. 8, after the semicircular hydrogel WG in the cell observation area 2 is cured by light, the immune cell IC can migrate within the photocured semicircular hydrogel WG and its migration direction is MD.

Compared with the conventional orifice plate test that the cells vertically migrate from top to bottom, the invention can effectively avoid the influence of gravity through this design, so that subsequent experimental results, such as the number and distance of immune cell IC migration, can be quantified for measurement to obtain the lateral displacement distance of the immune cell IC and the migration distance at different time points, so it can effectively simulate the effect of different drugs in the human body on the tumor microenvironment under different reaction times, which can greatly improve the efficiency and accuracy of drug screening.

Compared with the prior art, the array platform for three-dimensional cell culturing and drug testing and screening proposed in the invention can achieve the following advantages and effects:

(1) Construction of tumor microenvironment: using microfluidic structure combined with three-dimensional hydrogel and automatic co-arrangement of different types of cells to co-culturing different types of cells to completely simulate the tumor microenvironment in the body of the patient.

(2) Construction of the cell co-arrangement platform: design by calculating the effects of the size and frequency of the electric field generated by the electrode, so that it can imitate the different cell composition of histology, automatically arrange the plurality kinds of cells, and simulate the mutual influence of the plurality kinds of cells in the growth process to improve the shortcomings of single cell culturing.

(3) Automatically capture and quantify the number of cells: different numbers and properties of cells can be captured through differences in electrode patterns, which can be applied to simulate tumor sizes of different degrees.

(4) Dynamic injection system: The dynamic injection system is used to replace the culturing medium, so that the cells can grow effectively.

(5) Quantification of the number and distance of cell migration: by curing the semi-circular hydrogel, subsequent experimental results, such as the number and distance of immune cell migration, can be quantified, compared to the conventional holes plate test that cells migrate vertically from top to bottom, through this design, the invention can effectively avoid the influence of gravitation and measure the lateral displacement distance of immune cells and their migration distance at different time points, so as to simulate the effects on the tumor microenvironment under different drugs and different reaction times in human body, therefore, the efficiency and accuracy of drug screening can be greatly improved.

What is claimed is:

1. An array platform for three-dimensional cell culturing and drug testing and screening, comprising:
   a hydrogel-cell mixture injection area, configured to inject a plurality of kinds of hydrogel-cell mixtures;
   a plurality of cell observation areas, connected with the hydrogel-cell mixture injection area, wherein electrodes are disposed under the plurality of cell observation areas, and the plurality of hydrogel-cell mixtures in the plurality of cell observation areas are automatically quantified and three-dimensional cell co-arranged through the electrodes to imitate a structure of tissues in body;

a drug injection area, configured to inject a plurality of kinds drugs; and a plurality of drug combination generators, corresponding to the plurality of cell observation areas respectively and all connected with the drug injection area, configured to generate a plurality of drug combinations according to the plurality of drugs, wherein each of the plurality of the drug combination generators has a microfluidic channel structure;

wherein the electrodes comprise a plurality of first electrode partitions, a plurality of second electrode partitions and a plurality of third electrode partitions, the plurality of first electrode partitions is connected to each other, the plurality of second electrode partitions is connected to each other and the plurality of third electrode partitions is connected to each other, the plurality of first electrode partitions, the plurality of second electrode partitions and the plurality of third electrode partitions all have the same shape, and at least part of the plurality of first electrode partitions, the plurality of second electrode partitions and the plurality of third electrode partitions are arranged staggered with each other, liquid dielectrophoresis technology is used through the plurality of first electrode partitions and the plurality of second electrode partitions to simultaneously cultivate the plurality of hydrogel-cell mixtures and observe cell interactions under the plurality of drug combinations.

2. The array platform for three-dimensional cell culturing and drug testing and screening of claim 1, further comprising:

a culturing solution injection area; and a culturing solution recycling area;

wherein a culturing solution flowing out from the culturing solution injection area flows through the plurality of cell observation areas through a microfluidic channel to wash off excess hydrogel and cells, and then flows to the culturing solution recycling area.

3. The array platform for three-dimensional cell culturing and drug testing and screening of claim 2, wherein a shape of the microfluidic channel and an order and a winding method of the microfluidic channel passing through the plurality of cell observation areas are variable.

4. The array platform for three-dimensional cell culturing and drug testing and screening of claim 1, further comprising:

micropillars, configured to prevent hydrogels from being washed away during dynamic injection.

5. The array platform for three-dimensional cell culturing and drug testing and screening of claim 1, further comprising:

a buffer solution injection area, connected to the drug combination generator and configured to inject buffer solution.

6. The array platform for three-dimensional cell culturing and drug testing and screening of claim 1, wherein when the plurality of hydrogel-cell mixtures has been arranged in a specific position by the electrodes using liquid dielectrophoresis technology, the plurality of hydrogel-cell mixtures is directly cured by light in a large area without a photomask to imitate a structure of body tissues.

7. The array platform for three-dimensional cell culturing and drug testing and screening of claim 6, wherein size and response frequency of an electric field generated by the electrodes are used to imitate a composition of cancer tumors of different progressions and automatically arrange the plurality of kinds of cells in the plurality of kinds of hydrogel-cell mixtures, thereby simulating characteristics of mutual influence among the plurality of kinds of cells during a growth process to improve shortcomings of cultivating a single cell.

8. The array platform for three-dimensional cell culturing and drug testing and screening of claim 1, wherein a pattern size of the electrodes is used to distinguish disease progression of body tissues.

9. The array platform for three-dimensional cell culturing and drug testing and screening of claim 1, wherein an arrangement of the plurality of cell observation areas is symmetrical to the hydrogel-cell mixture injection area, and the hydrogel-cell mixture injection area is connected to the plurality of cell observation areas radially outward.

* * * * *